(12) United States Patent
Hisanaga et al.

(10) Patent No.: US 8,260,810 B2
(45) Date of Patent: Sep. 4, 2012

(54) CASE IMAGE REGISTRATION APPARATUS, METHOD AND RECORDING MEDIUM, AND CASE IMAGE SEARCH APPARATUS, METHOD, RECORDING MEDIUM AND SYSTEM

(75) Inventors: Ryuji Hisanaga, Kanagawa (JP); Akira Oosawa, Kanagawa (JP); Hiroyoshi Furukawa, Shizuoka (JP); Masahiro Endo, Shizuoka (JP); Masahiro Akimaru, Shizuoka (JP); Ken Yamaguchi, Shizuoka (JP)

(73) Assignees: FUJIFILM Corporation, Tokyo (JP); Shizuoka Prefecture, Shizuoka (JP)

( * ) Notice: Subject to any disclaimer, the term of this patent is extended or adjusted under 35 U.S.C. 154(b) by 182 days.

(21) Appl. No.: 12/720,420

(22) Filed: Mar. 9, 2010

(65) Prior Publication Data

US 2010/0228727 A1 Sep. 9, 2010

(30) Foreign Application Priority Data

Mar. 9, 2009 (JP) ................................. 2009-055622

(51) Int. Cl.
*G06F 17/30* (2006.01)
(52) U.S. Cl. ................... 707/772; 707/769; 382/305
(58) Field of Classification Search .................. 707/769, 707/772; 382/305
See application file for complete search history.

(56) References Cited

U.S. PATENT DOCUMENTS

| 7,374,077 | B2 | 5/2008 | Shimura | |
|---|---|---|---|---|
| 2006/0004278 | A1* | 1/2006 | Giger et al. | 600/408 |
| 2008/0068456 | A1* | 3/2008 | Fujii et al. | 348/130 |
| 2008/0075348 | A1* | 3/2008 | Rappaport et al. | 382/132 |
| 2008/0243395 | A1* | 10/2008 | Oosawa et al. | 702/19 |
| 2008/0247619 | A1 | 10/2008 | Li | |
| 2010/0166321 | A1* | 7/2010 | Sawant et al. | 382/209 |

FOREIGN PATENT DOCUMENTS

| JP | 2001-117936 A | 4/2001 |
|---|---|---|
| JP | 2004-005364 A | 1/2004 |
| JP | 2008-245719 A | 10/2008 |
| JP | 2008-257292 A | 10/2008 |

OTHER PUBLICATIONS

T.F. Cootes, et al., "Active Appearance Models," In Proc. 5th European Conference on Computer Vision, 1998, pp. 484-498, vol. 2, Springer Germany.

* cited by examiner

*Primary Examiner* — Khanh Pham
(74) *Attorney, Agent, or Firm* — Sughrue Mion, PLLC

(57) ABSTRACT

Case images are registered so as not to cause bias (or partiality or imbalance) in amounts of feature of the case images included in a database of a similar image search system for image diagnosis. Since registration of the case images to the database is controlled according to degrees of similarity of the amounts of feature, it is possible to prevent a lot of similar case images from being included in the search result. Thus, it is possible to reduce possibility of representing a similar search result which may interfere with an accurate diagnosis by a diagnostician.

12 Claims, 2 Drawing Sheets

FIG.3

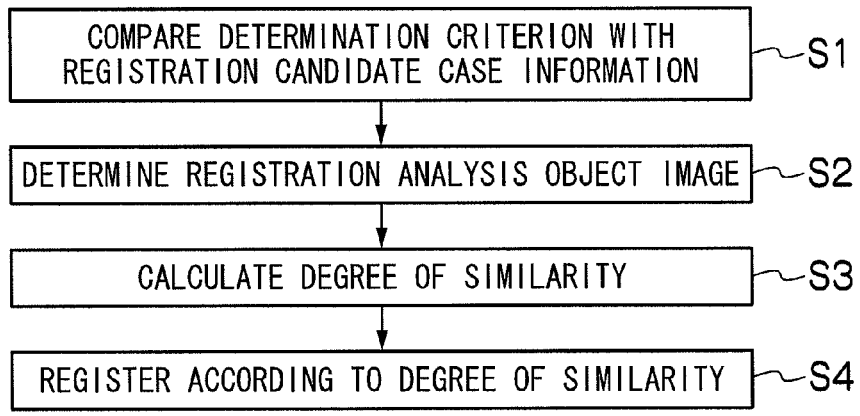

FIG.4

| VIEW POINT | DATA INCLUDING CRITERION |
|---|---|
| NAME, SEX AND AGE OF PATIENT | HEADER INFORMATION OF IMAGE DATA AND REPORT |
| IMAGING APPARATUS AND IMAGING CONDITION | HEADER INFORMATION OF IMAGE DATA AND REPORT |
| FINDING AND DISEASE NAME | REPORT INFORMATION |
| IMAGING PURPOSE (EX., SCREENING, FOLLOW-UP OR PRE-OPERATION) | HEADER INFORMATION OF IMAGE DATA, REPORT |
| ANATOMIC POSITION | HEADER INFORMATION OF IMAGE DATA, REPORT AND IMAGE ANALYSIS RESULT |
| PART | HEADER INFORMATION OF IMAGE DATA, REPORT AND IMAGE ANALYSIS RESULT |

CASE IMAGE REGISTRATION APPARATUS, METHOD AND RECORDING MEDIUM, AND CASE IMAGE SEARCH APPARATUS, METHOD, RECORDING MEDIUM AND SYSTEM

BACKGROUND OF THE INVENTION

1. Field of the Invention

The presently disclosed subject matter relates to a technique that retrieves and presents a case image similar to a diagnostic object image (image of object to be diagnosed) on the basis of an amount of feature (feature amount) extracted from the diagnostic object image.

2. Description of the Related Art

In Japanese Patent Application Laid-Open No. 2004-5364, an ROI (region of interest) is specified on image data; information such as image data which has a similar feature and a diagnostic result of the similar image data are retrieved from a database and displayed.

In Japanese Patent Application Laid-Open No. 2001-117936, a region of interest is extracted from a diagnostic image, and a similarity search is performed using the amount of feature of the region of interest.

Japanese Patent Application Laid-Open No. 2008-257292 shows another example of similar image search system.

Japanese Patent Application Laid-Open No. 2008-245719 shows an example of a technique for extracting a lesion region on the basis of position information of a region of interest.

T. F. Cootes, G. J. Edwards, and C. J. Taylor "Active Appearance Models", In Proc. 5th European Conference on Computer Vision, Springer Germany, volume II: pp. 484-498 (1998), shows a method of acquiring shape information and texture information of a lesion part in the ROI (region of interest).

SUMMARY OF THE INVENTION

In an image search system for image diagnosis according to the conventional technique, when a bias (or partiality or imbalance) occurs between data in a database and distribution of the amount of feature, the bias may adversely affect diagnosis of doctors. For example, for lungs, when an image search (image retrieval) is performed for a benign lesion such as inflammation whose feature in the image is similar to pulmonary cancer cases through a database including extremely many pulmonary cancer cases whose amounts of feature are similar to each other, most of cases obtained by the retrieval as being very similar to the benign lesion are pulmonary cancer cases. Therefore, when a doctor with inadequate experience uses that retrieval result to diagnose the case, the usage of the retrieval result prevents him/her from adequately diagnosing an inflammation even though the doctor suspects an inflammation before the retrieval.

In addition, in a case of collecting data of various types of image findings sharing the name of disease (disease name), such as pulmonary adenocarcinoma, when the disease name, or adenocarcinoma, is used as a criteria, image findings with the similar amounts of feature may be gathered. As a result, if 90% or more of the cases have the similar amounts of feature even with collection of 100 adenocarcinoma cases, accuracy of similarity search for adenocarcinoma on the residual 10% of adenocarcinoma cases is decreased, thereby adversary affecting the diagnosis of doctors.

The presently disclosed subject matter can register case images so as not to cause a bias (or partiality or imbalance) in amounts of feature of case images included in a database for a similar image search system for image diagnosis.

A case image registration apparatus according to the presently disclosed subject matter includes: a determination unit which compares case information corresponding to an object image, which is a case image to be determined whether registration to a database is required or not, and an amount of feature of the object image, with case information corresponding to a registered image, which is a case image other than the object image and has been registered in the database, and an amount of feature of the registered image, and determines whether to register the object image in the database or not according to a result of the comparison; and a registration unit which registers the object image when the determination unit determines to register the object image in the database.

Preferably, the case image registration apparatus further includes a degree of similarity calculation unit which calculates a degree of similarity between the amount of feature of the object image and the amount of feature of the registered image, and the determination unit determines whether to store the object image in the database or not according to the comparison of the degree of similarity with a prescribed registered determination threshold.

Preferably, the case image registration apparatus further includes a registration determination threshold calculation unit which calculates the prescribed registration determination threshold using a function whose variable is the total number of the case images registered in the database.

Preferably, the case image registration apparatus further includes an item determination unit which collates the case information corresponding to the object image and the case information corresponding to the registered image with each other on an item by item basis, and determines whether the number of matching items in the collation exceeds a prescribed number threshold or not, and the degree of similarity calculation unit, when the item determination unit determines that the number of matching items having exceeds the prescribed number threshold, calculates the degree of similarity between the amount of feature of the object image and the amount of feature of the registered image.

Preferably, the item of the case information includes at least any one of: information pertaining to a patient including the name, sex, age and other information of the patient; information pertaining to imaging including a type of an imaging apparatus, an imaging condition and other information; information pertaining to diagnosis including a finding, a disease name and other information; a lesion position; and an anatomic position of the lesion position.

Preferably, the object image is the case image inputted from an imaging apparatus or the case image having been registered in the database.

Preferably, the registration unit deletes any one of the registered image and the object image if the object image is the case image having been registered in the database.

A case image search apparatus according to the presently disclosed subject matter includes a search unit which compares a first amount of feature, which is an amount of feature corresponding to an image to be diagnosed with a second amount of feature corresponding to a case image in a database which has been registered by the case image registration apparatus according to claim 1, and searches the database for a case image having an amount of feature similar to the first amount of feature based on a result of the comparison.

Preferably, the search unit compares only the second amount of feature corresponding to an image which has determined to register in the database by the determination unit, with the first amount of feature.

Preferably, the case image search apparatus further comprises an output unit which outputs the case image retrieved by the search unit.

A case image search system according to the presently disclosed subject matter includes: the case image registration apparatus described above; and a case image search apparatus which comprises a search unit which compares a first amount of feature, which is an amount of feature corresponding to an image to be diagnosed with a second amount of feature corresponding to a case image in a database which has been registered by the case image registration apparatus, and searches the database for a case image having an amount of feature similar to the first amount of feature based on a result of the comparison.

A case image registration method performed by one or more computers according to the presently disclosed subject matter, the case image registration method, includes the steps of: comparing case information corresponding to an object image, which is a case image to be determined whether registration to a database is required or not, and an amount of feature of the object image, with case information corresponding to a registered image, which is a case image other than the object image and has been registered in the database, and an amount of feature of the registered image; determining whether to register the object image in the database or not according to a result of the comparison; and registering the object image in the database based on a result of the determination.

A recording medium, on which a program causing one or more computers to perform the case image registration method is recorded, is also included in the presently disclosed subject matter.

A case image search method performed by one or more computers according to the presently disclosed subject matter, includes the steps of: comparing a first amount of feature, which is an amount of feature corresponding to an image to be diagnosed with a second amount of feature corresponding to a case image in a database which has been registered by the case image registration method described above; and searching the database for a case image having an amount of feature similar to the first amount of feature based on a result of the comparison.

A recording medium, on which a program causing one or more computers to perform the case image search method is recorded, is also included in the presently disclosed subject matter.

According to the presently disclosed subject matter, since the registration of the case images to the database is controlled according to the degrees of similarity of the amounts of feature, it is possible to prevent a lot of similar case images from being included in the search result. Thus, it is possible to reduce possibility of representing a similar search result which may interfere with an accurate diagnosis by a diagnostician.

BRIEF DESCRIPTION OF THE DRAWINGS

FIG. 3 is a flowchart for explaining a registration process;
and
FIG. 4 is a diagram showing an example of a determination criterion.

DETAILED DESCRIPTION OF THE PREFERRED EMBODIMENTS

Figure 1:
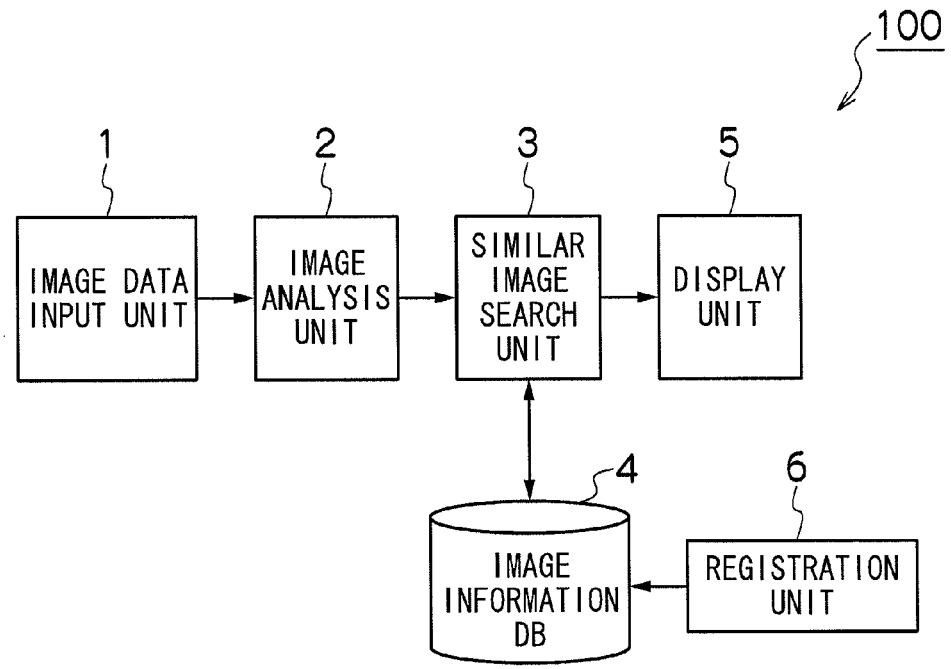
FIG. 1 is a schematic configuration diagram of a similar case image search system.

FIG. 1 is a schematic configuration diagram of a similar case image search system 100 according to a preferred embodiment of the presently disclosed subject matter. This system includes an image data input unit 1, an image analysis unit 2, a similar image search unit 3, an image information DB 4, a display unit 5, and a registration unit 6. The similar case image search system 100 may be configured with a computer (including: circuits required for operational processing such as a CPU, RAM and ROM, a data recording medium, a data input and output circuit, a display circuit, an operation device, and a communication circuit).

The each block of the similar case image search system 100 may integrally be configured in one computer. Instead, the similar case image search system 100 may be configured such that the blocks are configured with separate computers and the computers are connected to each other via a network. The image analysis unit 2, the similar image search unit 3 and the registration unit 6 may be replaced with program modules (stored in a computer readable medium such as a ROM) to be performed on a computer; special hardware configurations are not necessarily required. The display unit 5 may be configured with a liquid crystal display. The image information DB 4 may be configured with a hard disk, for example.

The image data input unit 1 inputs diagnostic object images (query images), such as a CT (Computer Tomography) image, an MRI (Magnetic Resonance Imaging) image, a PET (Positron Emission Tomography) image, an X ray image (including a CR (Computed Radiography) image), a US (ultrasonic) image, an endoscopic image, a mammography image, and a pathological image. The image data input unit 1 can input supplementary information, such as the image size and the imaged date and time, and case information, along with these query images. Communication protocols between the image data input unit 1 and a medical diagnostic imaging apparatus and formats of the query images and the supplementary information are compliant with a prescribed standards such as a DICOM (Digital Imaging and Communication in Medicine).

The image analysis unit 2 analyzes a query image inputted from the image data input unit 1, and creates an amount of feature (a first amount of feature) required to retrieve similar images accumulated in the image information DB 4. A method for creating the amount of feature is performed in a similar manner to that of an image analysis unit 21, which will be described later.

The similar image search unit 3 compares the first amount of feature created by the image analysis unit 2 and the amount of feature (second amount of feature) of case image accumulated in the image information DB 4 with each other, and calculates a degree of similarity therebetween. The second amount of feature has been created beforehand from the case image according to a method which is the same as the calculation method adopted in the image analysis unit 2, and accumulated. The similar image search unit 3 specifies the case image corresponding to the second amount of feature whose similarity with information on the amount of feature of the query image is the highest among the entire case images accumulated in the image information DB 4 or the case images corresponding to a part designated beforehand from the operation device. The similar image search unit 3 then displays, on the display unit, 5 the specified case image and the various types of case information which is accumulated in the image information DB 4 and corresponding to the case image.

The display unit 5 may be replaced with another output device other than the image output device. For example, the specified case image and the various types of information corresponding to the case image, which are accumulated in the image information DB 4, may be outputted by a printing device, instead of the display unit 5 or along with the display unit 5. If a search result is not image information, the result can be outputted by synthesized voice output and the like from an audio output device. Instead, the output device may be a network I/F, and the search result may be outputted to a desired communication terminal (a personal computer, a cellular phone, a PDA (Personal Digital Assistance), etc.).

The image information DB 4 includes case information having case images to be search object images. Here, the case information may be stored in a manner classified according to diseases. Further, statistical information and disease information on a disease-by-disease basis, and disease information of an error-prone disease and medical information with respect to a specific disease may be linked and stored.

The case information also includes text-based diagnostic information such as diagnostic reports created by radiologists in addition to the case image of each definitely diagnosed disease.

The statistical information on a disease-by-disease basis includes, for example, following information:
- degree of similarity of a representative case (the highest similarity in a disease);
- average degree of similarity;
- total number of registered cases of the disease concerned in a case DB;
- the number of registered cases similar to the representative cases (case patterns);
- characteristics of the case pattern . . . leading symptoms;
- characteristics of patients in the case pattern . . . average age, medical history, history of smoking, etc.;
- national and regional morbidity rate; and
- miscellaneous.

The image information DB 4 includes the amounts of feature (second amount of feature) extracted from lesion parts of respective registered case images. However, if the case image itself is stored in the image information DB 4, the second amount of feature can be acquired by subsequently analyzing the case image by the image analysis unit 2 or the like. Accordingly, registration of the second amount of feature in the image information DB 4 is not necessarily required to implement of the presently disclosed subject matter.

The display unit 5 may display statistic information such as search result of similar images on a disease-by-disease basis from similar images in the database, in addition to the image data with a high degree of similarity.

The case image to be registered in the image information DB 4 by the registration unit 6 can be acquired by means of imaging apparatuses (CT apparatus, MRI apparatus, PET apparatus, X-ray apparatus, US apparatus, endoscope, mammography apparatus, camera for a microscope, etc.) as with a query image. The second amount of feature corresponding to the case image registered in the image information DB 4 by the registration unit 6 is acquired by the image analysis similar to that in the image analysis unit 2. The case information corresponding to the case image registered in the image information DB 4 by the registration unit 6 is acquired by a user's input operation via an operation device and the like. In this embodiment, the registration unit 6 performs registration so as not to cause a bias (or partiality or imbalance) in the amount of feature of the image data included in the image information DB 4.

Figure 2:
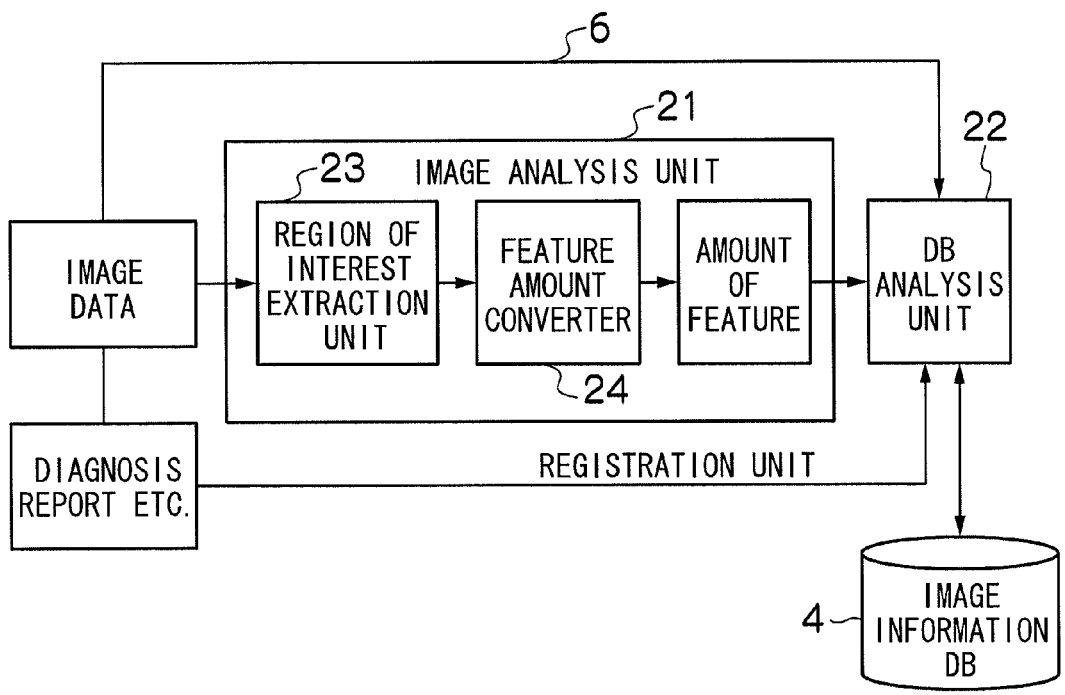
FIG. 2 is a block diagram showing a registration unit in detail.

FIG. 2 shows the registration unit 6 in detail. The registration unit 6 includes the image analysis unit 21 and a DB analysis unit 22. The image analysis unit 21 includes a region of interest extraction unit 23 and a feature amount converter 24. The respective blocks of the registration unit 6 may integrally be configured into a computer. Instead, the registration unit 6 may be configured such that the blocks are configured with separate computers and the computers are connected to each other via a network. The DB analysis unit 22, the region of interest extraction unit 23 and the feature amount converter 24 may be replaced with program modules (stored in a computer-readable recording medium such as a ROM) to be performed on a computer; special hardware configurations are not necessarily required.

The image analysis unit 21 inputs desired case images, such as a CT image, an MRI image, a PET image, an X ray image (including a CR image), an US (ultrasonic) image, an endoscopic image, and a pathological image, as registration candidate images. The image analysis unit 21 also inputs case information corresponding to registration candidate images.

The region of interest extraction unit 23 extracts a part to be retrieved, or the region of interest, such as a lesion, organ or the like included in the case image, from the inputted registration candidate images. A method for extracting the region of interest is arbitrary. For example, a publicly known image processing technique using features of contours, pixel values and position information of an image, such as automatic extracting methods of Japanese Patent Applications Laid-Open Nos. 2004-5364 and 2001-117936, and a method for extracting a region on the basis of the position information of the region of interest of Japanese Patent Application Laid-Open No. 2008-245719 and the like, may be used. The extraction of the region of interest is not necessarily full automatic. Instead, the extraction may semi-automatically be performed by an image processing technique that uses features in proximity to a region designated through an operation device by the user.

Next, the feature amount converter 24 calculates the amount of feature on an extracted region extracted by the region of interest extraction unit 23. The amount of feature to be calculated may be an amount of feature pertaining to pixel values such as the average, the variance, the maximum value, the minimum value and the luminance histogram of image data, and/or the amount of feature pertaining to the shape such as the position of the extracted region, the roundness of the extracted region, the moment, the radius of a section, the volume and the area. In addition thereto, the feature amount may be shape information and/or texture information of the lesion in the ROI (region of interest) acquired by "Active Appearance Models" (T. F. Cootes et al). Instead, information temporarily registered in the image information DB 4 may be processed using a prescribed mathematical expression (e.g., principal component analysis and independent component analysis) and the obtained value may be adopted as the amount of feature.

The DB analysis unit 22 determines whether the registration candidate image is to be registered in the image information DB 4 or not, on the basis of the amounts of feature of the registration candidate images calculated by the feature amount converter 24 and the amounts of feature of case images accumulated in the image information DB 4. The DB analysis unit 22 registers the registration candidate image in the image information DB 4 or discards the image without registration according to the determination result.

More specifically, the DB analysis unit 22 performs a registration process as shown in FIG. 3.

In step S1, the DB analysis unit 22 compares the case information (determination criterion) corresponding to any one of case images having already been registered in the image information DB 4 and the case information (registration candidate case information) corresponding to the registration candidate image with each other, and determines whether both are identical with each other or not. FIG. 4 shows an example of the determination criterion. The criterion includes: information pertaining to a patient, such as the name, age and sex of the patient; information pertaining to imaging, such as the type (CT, MRI, etc.) and the model number of the apparatus used for imaging and an imaging condition; information pertaining to the definite diagnosis such as the finding, the disease name and the others; the purpose of imaging; the anatomic position of the lesion part; and the part of the lesion (organ), which are indicated by report information stored in a header and the like of the image data. Determination (Matching) of identity between the determination criterion and the registration candidate case information is performed with respect to respective items included in the case information. In addition thereto, presence or absence of a certain qualification (a certified physician or a specialist physician) of the person who has registered the diagnostic information, the volume of report information, the imaging date and time of the image, the registration date and time of the case information and the like may also be adopted as the determination criterion.

Based on the result of the matching in step S1, in step S2, the DB analysis unit 22 counts the number of items whose contents are determined to be identical in step S1. If the number exceeds a first threshold designated beforehand by a user's operation via the operation device, the registration candidate image corresponding to the registration candidate case information is determined as a registration analysis object image; the processing proceeds to step S3. Here, a registration analysis object image means an image which is to be analyzed in order to determine whether the image is to be registered in the image information DB 4.

For example, when the threshold=3, and if case information of a certain determination criterion and case information of the registration candidate case information are identical all in the age of the patient, the imaging condition and the anatomic position, the registration candidate image corresponding to the registration candidate case information is determined as a registration analysis object image.

However, if at least the disease name included in the determination criterion and the disease name included in the registration candidate case information are identical with each other, the registration candidate image is unconditionally determined as the registration analysis object image; the processing proceeds to step S3. This is for eliminating redundant registration of the image with the same disease name and the similar image finding.

In analogous terms, if at least the disease name included in the determination criterion and the disease name included in the registration candidate case information are not identical with each other, the registration candidate image is unconditionally determined as an image to be registered. In this case, step S3 is omitted and the processing proceeds to step S4.

In step S3, the DB analysis unit 22 calculates a degree of similarity between the amount of feature of the registration analysis object image calculated by the feature amount converter 24 and the amount of feature of the case image corresponding to the case information storing the determination criterion identical with the registration analysis object image. The feature amount converter 24 may omit an analysis of an image other than the registration analysis object image. A publicly known method, for example a difference of values of the amounts of feature and the least squares methods in a feature space (a weighted space is acceptable), may be adopted as a method for calculating the degree of similarity. For the sake of convenience of illustration, the degree of similarity S is defined by the following mathematical expression (mathematical expression descried in the paragraph 0048 of Japanese Patent Application Laid-Open No. 2008-257292). Note that implementation of the presently disclosed subject matter does not limit the calculation norm of the degree of similarity S to this definition.

$$S = \sum_{i=1}^{n} wi|Mi - mi|$$ [Expression 1]

The amount of feature $m_i$ (i=1, 2, ..., n) is the amount of feature of the registered case image. $M_i$ (i=1, 2, ..., n) is the amount of feature extracted from the registration analysis object image. $w_i$ (i=1, 2, ..., n) is a weighting coefficient corresponding to each amount of feature having been defined beforehand, on disease-by-disease basis. Numerical subscript "i" of $m_i$, $M_i$ and $w_i$ designates a coordinate in a feature amount space. The more similar both amounts of feature, the smaller the value of the degree of similarity S becomes; the more different both amounts of feature, the larger the value of the degree of similarity S becomes.

Preferably, in step S1, if the disease name included in the determination criterion and the disease name included in the registration candidate case information are identical and the parts and the anatomic positions of lesion are both identical, the registration candidate image may be unconditionally determined as the registration analysis object image. In this case, it is possible to prevent the amounts of feature of parts irrelevant to each other from being compared in step S3. For example, if the amount of feature $m_i$ (i=1, 2, ..., n) extracted from the registration analysis object image is a value (n-dimensional multi-valued data) pertaining to a lung area S1 (the part and the analytical position), the feature amount $M_i$ (i=1, 2, ..., n) of the registered image whose degree of similarity S is to be calculated is also a value (n-dimensional multi-valued data) pertaining to the lung area S1.

In step S4, if the calculated degree of similarity is less than a prescribed second threshold, the DB analysis unit 22 determines that the registration analysis object image is out of scope of registration and does not register the image in the image information DB 4; if the calculated degree of similarity is not less than the prescribed second threshold, the DB analysis unit 22 determines that the registration analysis object image is the image to be registered and registers the image in the image information DB 4. In this case, the case information corresponding to the register analysis object image is also registered in the image information DB 4.

The second threshold TH is, for example, determined according to a following mathematical expression, $$TH = \alpha \times N + \beta.$$

N is the total number of case images registered in the image information DB 4. The $\alpha$ and $\beta$ are constants. The $\alpha$, $\beta$ and/or the threshold themselves may arbitrarily be designated by a user's input operation via the operation device. Typically, TH=f(N). "f" is any function which tends to increase according to increase of N. The function "f" may arbitrarily be designated by a user's input operation via the operation device, and the processing unit (CPU) may calculate the actual second threshold according to the designated function.

More specifically, if the number of registered case images is small, the second threshold becomes small and the registration analysis object image whose degree of similarity with the registered case image is a relatively small value (high correlation) is registered. If number of registered case images is large, the second threshold becomes large and the registration analysis object image having a high correlation with the registered case image becomes not to be registered. Instead, if the number of registration N is less than a certain threshold (e.g., 100), the registration analysis object image and its case information may unconditionally be registered. That is, if the number of registration is small, enrichment of the image information DB 4 may take precedence.

In lieu of not registering the image determined not to be registered, the registered image and the corresponding case image in the image information DB 4 whose degree of similarity with the image determined not to be registered is less than the second threshold may be deleted, and the image determined not to be registered and its corresponding case information may be registered instead. This prevents the images having similar feature from being redundant in the image information DB 4. Selection of whether the image determined not to be registered is not actually registered or the image is substituted for the registered case image may be arbitrarily designated by a user's operation to the operation device and any one of the images may be registered in the image information DB 4 according to the designation. Instead, if the case information of the registered case image includes information with high precedence, such as new date and time information, report information with high content, registration by a qualified person, or large amount of image data, the registered case image may be left in the image information DB 4. Conversely, if the case information of the registered case image includes no information with high precedence, the registered case image may be deleted from the image information DB 4, and the image determined not to be registered may newly be registered in the image information DB 4.

The registration candidate image is not necessarily a newly inputted image, and may be the image arbitrarily selected from among the case images registered in the image information DB 4. In this case, the registration unit 6 leaves the image when it is determined that the image is to be registered in the image information DB 4, and deletes the image from the image information DB 4 when it is determined that the image is not to be registered. As with the above description, if the case information includes information with high precedence, the case image corresponding thereto may be left in the image information DB 4, and if the case information does not include information with high priority, the case image corresponding thereto may be deleted from the image information DB 4. In other words, if there are two images whose degree of similarity is less than the second threshold, only any one of both may be deleted.

In general, if there are two or more images in the image information DB 4, the degree of similarity is calculated from a pair composed of any two different images in the image information DB 4, and any one image of the pair is deleted according to result of the comparison between the value of the degree of similarity and the second threshold; if this process is comprehensively repeated over all pairs of images in the image information DB 4, redundancy of the similar images can be eliminated among the images having already been registered in the image information DB 4. This may be performed by user's designation of a command such as "refresh the image information DB 4" through the operation device. Instead, this may periodically be performed at a desired schedule.

In addition, an image determined not to be registered may be registered in the image information DB 4 along with a flag indicating that the image is determined not to be registered, and subsequently the case image assigned with the flag is excluded from the images to be searched by the similar image search unit 3. Accordingly, the similar image search unit 3 retrieves similar images only from the images without the flag. In other words, the similar image search unit 3 compares only the second amount of feature of the case images without the flag with the first amount of feature.

As described above, since the registration of the case images to the image information DB 4 is controlled according to the degrees of similarity of the amounts of feature, it is possible to prevent a lot of similar case images from being retrieved as the search result. Thus, it is possible to reduce possibility of representing a similar search result which may interfere in diagnosis by a diagnostician.

While examples and embodiments of the presently disclosed subject matter have been explained in detail, the presently disclosed subject matter is not limited to the above, needless to say, various improvements and modifications may be added without departing from the scope of the presently disclosed subject matter.

For example, by providing a program causing a computer to execute the processes performed devices according to the embodiments, recording the program on a recording medium, installing the program on a computer using the recording medium, and causing the computer on which the program is installed to execute the program, it is possible to implement the devices according to the embodiments.

What is claimed is:

1. A case image registration apparatus comprising:
   a determination unit including at least one processor which compares case information corresponding to an object image, which is a case image to be determined whether registration to a database is required or not, and an amount of feature of the object image, with case information corresponding to a registered image, which is a case image other than the object image and has been registered in the database, and an amount of feature of the registered image, and determines whether to register the object image in the database or not according to a result of the comparison;
   a registration unit which registers the object image when the determination unit determines to register the object image in the database; and
   further comprising
   a degree of similarity calculation unit which calculates a degree of similarity between the amount of feature of the object image and the amount of feature of the registered image,
   wherein the determination unit determines whether to store the object image in the database or not according to the comparison of the degree of similarity with a prescribed registered determination threshold,
   an item determination unit which collates the case information corresponding to the object image and the case information corresponding to the registered image with each other on an item by item basis, and determines whether the number of matching items in the collation exceeds a prescribed number threshold or not,
   wherein the degree of similarity calculation unit, when the item determination unit determines that the number of matching items having exceeds the prescribed number threshold, calculates the degree of similarity between the amount of feature of the object image and the amount of feature of the registered image, and wherein the item of the case information includes at least any one of: information pertaining to a patient including the name, sex, age and other information of the patient; information pertaining to imaging including a type of an imaging apparatus, an imaging condition and other information; information pertaining to diagnosis including a finding, a disease name and other information; a lesion position; and an anatomic position of the lesion position.

2. The case image registration apparatus according to claim 1, further comprising a registration determination threshold calculation unit which calculates the prescribed registration determination threshold using a function whose variable is the total number of the case image registered in the database.

3. The case image registration apparatus according to claim 1, wherein the object image is the case image inputted from an imaging apparatus or the case image having been registered in the database.

4. The case image registration apparatus according to claim 3, wherein the registration unit deletes any one of the registered image and the object image when the object image is the case image having been registered in the database.

5. The case image registration apparatus of claim 1, further comprising:

a search unit which compares a first amount of feature, which is an amount of feature corresponding to an image to be diagnosed with a second amount of feature corresponding to a case image in a database which has been registered, and searches the database for a case image having an amount of feature similar to the first amount of feature based on a result of the comparison.

6. The case image registration apparatus according to claim 5, wherein the search unit compares only the second amount of feature corresponding to an image which has determined to register in a the database by the determination unit, with the first amount of feature.

7. The case image registration apparatus according to claim 5, further comprising:

an output unit which outputs the case image retrieved by the search unit.

8. A case image search system comprising:

a case image registration apparatus according to claim 1; and a case image search apparatus which comprises a search unit which compares a first amount of feature, which is an amount of feature corresponding to an image to be diagnosed with a second amount of feature corresponding to a case image in a database which has been registered by the case image registration apparatus, and searches the database for a case image having an amount of feature similar to the first amount of feature based on a result of the comparison.

9. A case image registration method performed by one or more computers, comprising the steps of:

comparing case information corresponding to an object image, which is a case image to be determined whether registration to a database is required or not, and an amount of feature of the object image, with case information corresponding to a registered image, which is a case image other than the object image and has been registered in the database, and an amount of feature of the registered image;

determining whether to register the object image in the database or not according to a result of the comparison;

registering the object image in the database based on a result of the determination, calculating a degree of similarity between the amount of feature of the object image and the amount of feature of the registered image, determining whether to store the object image in the database or not according to the comparison of the degree of similarity with a prescribed registered determination threshold, collating the case information corresponding to the object image and the case information corresponding to the registered image with each other on an item by item basis, and determining whether the number of matching items as a result of collation exceeds a prescribed number threshold or not, wherein when it is determined that the number of matching items exceeds the prescribed number threshold, calculating the degree of similarity between the amount of feature of the object image and the amount of feature of the registered image, and wherein the item of the case information includes at least any one of: information pertaining to a patient including the name, sex, age and other information of the patient; information pertaining to imaging including a type of an imaging apparatus, an imaging condition and other information; information pertaining to diagnosis including a finding, a disease name and other information; a lesion position; and an anatomic position of the lesion position.

10. A case image registration method of claim 9 performed by one or more computers, further comprising the steps of:

comparing a first amount of feature, which is an amount of feature corresponding to an image to be diagnosed with a second amount of feature corresponding to a case image in a database which has been registered; and searching the database for a case image having an amount of feature similar to the first amount of feature based on a result of the comparison.

11. A recording medium on which a program is recorded, the program comprising computer-executable instructions of:

comparing case information corresponding to an object image, which is a case image to be determined whether registration to a database is required or not, and an amount of feature of the object image, with case information corresponding to a registered image, which is a case image other than the object image and has been registered in the database, and an amount of feature of the registered image;

determining whether to register the object image in the database or not according to a result of the comparison;

registering the object image in the database based on a result of the determination, calculating a degree of similarity between the amount of feature of the object image and the amount of feature of the registered image, determining whether to store the object image in the database or not according to the comparison of the degree of similarity with a prescribed registered determination threshold, collating the case information corresponding to the object image and the case information corresponding to the registered image with each other on an item by item basis, and determining whether the number of matching items as a result of collation exceeds a prescribed number threshold or not, wherein when it is determined that the number of matching items exceeds the prescribed number threshold, calculating the degree of similarity between the amount of feature of the object image and the amount of feature of the registered image, and wherein the item of the case information includes at least any one of: information pertaining to a patient including the name, sex, age and other information of the patient; information pertaining to imaging including a type of an imaging apparatus, an imaging condition and other information; information pertaining to diagnosis including a finding, a disease name and other information; a lesion position; and an anatomic position of the lesion position.

12. A recording medium of claim 11, the program further comprising computer-executable instructions of:

comparing a first amount of feature, which is an amount of feature corresponding to an image to be diagnosed with a second amount of feature corresponding to a case image in a database which has been registered; and searching the database for a case image having an amount of feature similar to the first amount of feature based on a result of the comparison.

* * * * *